United States Patent [19]

Major et al.

[11] 4,021,493
[45] May 3, 1977

[54] VANILLIN RECOVERY PROCESS

[75] Inventors: Frederick William Major; Francois Marcel André Nicolle, both of Hawkesbury, Canada

[73] Assignee: Canadian International Paper Company, Montreal, Canada

[22] Filed: Sept. 8, 1975

[21] Appl. No.: 610,929

Related U.S. Application Data

[63] Continuation of Ser. No. 413,911, Nov. 8, 1973, abandoned.

[52] U.S. Cl. .......................................... 260/600 A
[51] Int. Cl.$^2$ ........................................ C07C 45/24
[58] Field of Search ................... 260/600 A, 507 R

[56] References Cited

UNITED STATES PATENTS

| | | | |
|---|---|---|---|
| 2,057,117 | 10/1936 | Sandborn et al. | 260/600 A |
| 3,049,566 | 8/1962 | Schoeffel | 260/600 A |

*Primary Examiner*—Bernard Helfin

[57] ABSTRACT

A process is provided for isolating vanillin from alkaline aqueous solutions containing unwanted, chemically-related phenolic impurities, such as orthovanillin, acetovanillone, para-hydroxybenzaldehyde, syringaldehyde and the like, wherein the alkaline aqueous solution is subjected to an extractive process including as a step, extractive bisulfitation. The step of extractive bisulfitation involves the formation of an alkali-metal bisulfite complex of vanillin in the presence of a substantially water-insoluble organic solvent, such as a water-insoluble alkanol, e.g., normal-butyl alcohol.

9 Claims, 3 Drawing Figures

VANILLIN RECOVERY PROCESS

This is a continuation of application Ser. No. 413,911, filed Nov. 8, 1973, now abandoned.

BACKGROUND OF THE INVENTION

The present invention relates to a process for isolating and purifying vanillin from aqueous alkaline solutions containing vanillin and related phenolic contaminants such as orthovanillin, acetovanillone, para-hydrobenzaldehyde, and syringaldehyde, and the like.

It is known that vanillin can be made by oxidizing a lignin or lignosulfonate material, such as results from the kraft and sulfite cooking processes for producing pulp. The oxidation is carried out at elevated temperatures and pressures in the presence of an oxygen-containing gas in an alkaline solution. The resulting alkaline aqueous solution contains in addition to the desired vanillin, the unwanted contaminants, such as orthovanillin, acetovanillone, para-hydroxybenzaldehyde and syringaldehyde, which must be removed from the vanillin if the vanillin is to be of high purity and quality.

Numerous processes have been proposed for purifying vanillin from alkaline solutions. These include Sandborn U.S. Pat. No. 2,104,701. This patent treats by countercurrent extraction the aqueous alkaline solution of vanillin with a suitable water-immiscible solvent, such as normal butyl alcohol, and recovers the solvent for reuse. The vanillin is removed from the solvent and is subjected to further purification by any known means, such as by distilling the solvent as its water-binary mixture to leave the vanillin compound in an alkaline aqueous solution for further refining.

Other patents employing butyl alcohol extractions include U.S. Pat. Nos. 2,399,607, 2,104,701 and 2,489,200. Other patents employ propyl alcohol or isopropyl alcohol as the extractant, such as U.S. Pat. No. 2,721,221.

Other patents disclosed purification of vanillin by employing distillation treatments such as U.S. Pat. Nos. 2,506,540 and 2,745,796.

While the foregoing treatments are useful in purifying vanillin, it is desired to provide improved processes which more efficiently and effectively isolate and separate vanillin from its chemically related contaminating impurities. Accordingly, it is an object of the present invention to provide an efficient and effective process for removing and purifying vanillin from aqueous alkaline solutions containing contaminants.

It is also an object of the present invention to provide highly efficient and economical procedures for purifying vanillin.

Other objects will be apparent to those skilled in the art from the present description taken in conjunction with the accompanying drawings, in which.

GENERAL DESCRIPTION OF INVENTION

Figure 1:
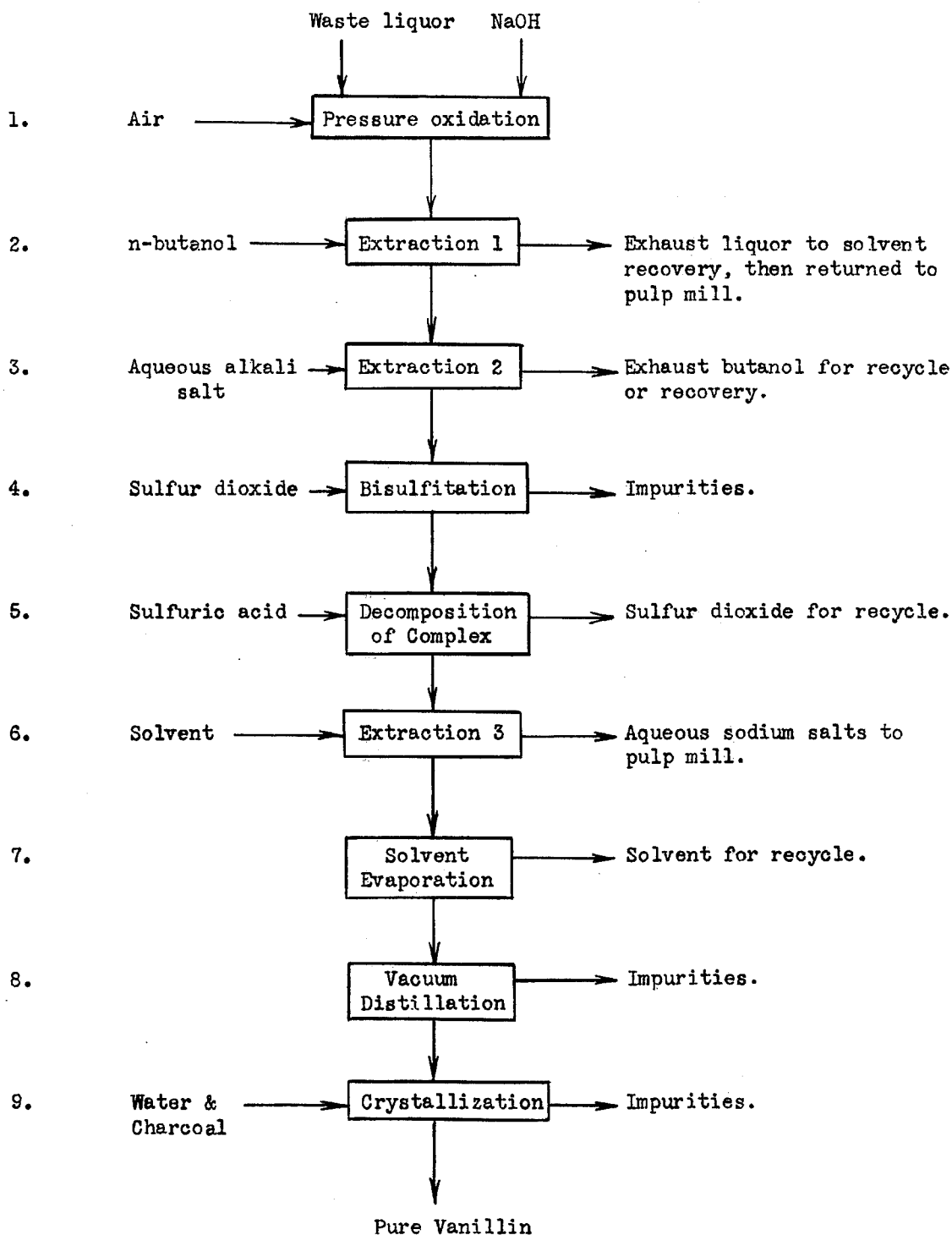
FIG. 1 is a flow diagram of the general scheme of the purification process of the present invention.

The process of the present invention is suitable for removing and purifying vanillin from aqueous alkaline solutions containing vanillin and related phenolic impurities. The process is suitable for recovery and purifying vanillin from the alkaline oxidation reaction solutions resulting from the alkaline oxidation of sulfite waste liquors and kraft black liquors. One type of alkaline solutions of vanillin to which the present invention is most suitable is that the alkaline oxidation reaction solutions obtained from kraft black liquors in accordance with concurrently filed U.S. application, Ser. No. 413,912, of Donald B. Mutton et al., entitled "Lignin Oxidation Process".

The product of the oxidation reaction of pulp waste liquors, whatever the conditions, is an exceedingly heterogeneous mixture. Many of the organic compounds, including the desired vanillin, are in the form of their sodium salts, in aqueous alkaline solution. In the industry, procedures have long been established for extracting the sodium salt of vanillin by means of a higher alcohol, such as normal butyl alcohol. See Sandborn U.S. Pat. No. 2,104,701, or isopropyl alcohol. See Bryan U.S. Pat. No. 2,692,291. The distribution coefficient of the sodium salt between water and butanol is in favour of water, and this entails considerable volumes of butanol and many stages of extraction if the vanillin is to be efficiently removed. The resulting solution of sodium vanillinate in butanol is dilute but represents a considerable purification step in itself when compared with the original reaction liquor. However, several additional purification stages are needed to separate vanillin of a grade suitable for food usage from the many similar, but unwanted, substances which accompany it in the butanol solution.

A second step in the purification procedure, which is also disclosed in said U.S. Pat. No. 2,104,701, and in U.S. Pat. No. 2,399,607, is the transfer of sodium vanillinate from its solution in butanol to an aqueous phase. By virtue of the superior solubility of the sodium salt in water, this transfer is effected very easily in a countercurrent extraction apparatus having relatively few theoretical stages. To minimize emulsification problems and to facilitate separation of the phases, earlier workers have found the incorporation of a low concentration of a sodium salt in the extracting water beneficial. Alkali hydroxide or alkali sulfate, such as sodium hydroxide or sodium sulfate, in the range of 3 to 5 grams per liter are suitable for this purpose. The proportion of extracting water may be chosen to be one half to one fifth the volume of the butanol solution, thereby accomplishing a desirable concentration effect. Little purification occurs during this second extraction, and the butanol phase, being relieved of most of its dissolved substances, is sufficiently pure to be recycled to the first extraction stage.

A further purification technique, disclosed in the prior art, makes use of the ability of aldehyde compounds such as vanillin to form water-soluble bisulfite complexes. (See Toppel U.S. Pat. No. 2,745,796 and U.S. Pat. No. 2,057,117.) They may thus be separated from those compounds which do not form such complexes and which remain either solvent-soluble or insoluble in water at the pH of bisulfitation.

In our own experience, the aqueous solution of sodium vanillinate arising from the second extraction stage carries with it sufficient sodium hydroxide to be strongly alkaline. At this pH, many unwanted acidic substances, including ligneous compounds of low molecular weight, remain in solution. During the bisulfitation operation, sulfur dioxide is blown into the alkaline solution, forming sodium bisulfite stoichiometrically in excess of that required to complex the aldehydic compounds present. The pH falls to a point between 3.5 and 4.0 where many of the non-reacting impurities out of solution. Usually, they are deposited on the walls of the reacting vessel in the form of troublesome gums or tars, while the aqueous solution of bisulfite complexes may be clouded by the same material held in emulsified suspension. An important feature of this invention is a process we have termed "extractive bisulfitation," in which the process of forming the busulfite complexes is carried out in the presence of an extracting solvent in a novel manner.

In essence, extractive bisulfitation involves the use of a solvent for entraining the gums and tars precipitated during the bisulfitation operation. However, when performed according to the method of our invention, it has the additional advantage of extracting in one operation and with the minimum of solvent those non-reacting impurities, such as acetovanillone, which are soluble in the aqueous solution of the bisulfite complex.

In the general scheme of our process, as shown in FIG. 1, kraft waste liquor is fortified with sodium hydroxide and then oxidized with air at elevated temperature and pressure. The oxidation product is extracted with a solvent (typically, normal butyl alcohol) and the exhausted waste liquor is returned to the mill after recovery of minor amounts of dissolved solvent. The solvent extract, containing crude vanillin as its sodium salt, is further extracted with an aqueous solution, thus transferring the sodium vanillinate back to an aqueous phase. By passing sulfur dioxide into this aqueous extract, aldehydic substances including vanillin are converted into their water-soluble bisulfite complexes. Other non-reacting substances are either rendered insoluble or may be solvent-extracted from the aqueous solution of bisulfite complexes. The purified complex solution is decomposed back into its components by acidifying to a low pH, preferably with sulfuric acid, when the sulfur dioxide which is evolved may be recycled for use again. After removal of all $SO_2$, the purified vanillin in the aqueous solution may be collected into a suitable solvent and concentrated by evaporation into a crystalline mass. Commonly, this is subjected to vacuum distillation, from which the vanillin-rich fraction is further purified by one or more crystallizations from water, using charcoal to adsorb last traces of impurities.

Figure 2:
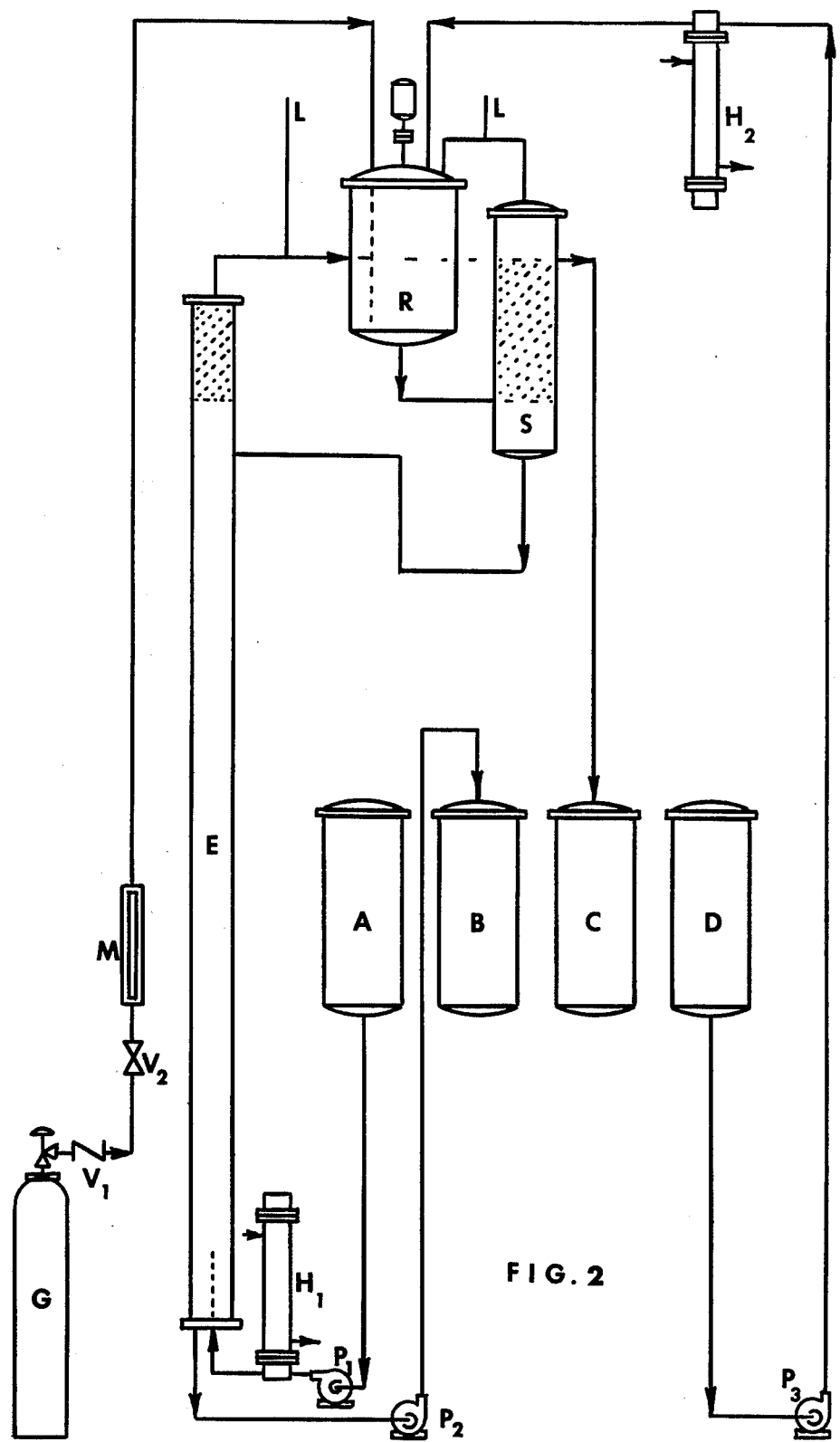
FIG. 2 is an illustrative flow diagram of one type of apparatus for employing the extractive bisulfitation process which is novel in our invention.

The extractive bisulfitation process may desirably be performed in an apparatus of the type illustrated in FIG. 2. Since the aqueous solution of sodium vanillinate to be bisulfited is already saturated with butanol from the second stage of extraction, it is convenient to use the same solvent as the entrainant during bisulfitation. In this case, the solvent forms the upper phase. In FIG. 2, aqueous sodium vanillinate solution is pumped from tank D by means of proportioning pump $P_3$, through heat exchanger $H_2$, where the temperature is adjusted to the required level, to the agitated reactor R. At the same time, sulfur dioxide is fed below the surface of the liquid in reactor R from gas cylinder G, via check valve $V_1$, control valve $V_2$, and flowmeter M. Also feeding into R is the upper butanol phase overflowing from the countercurrent extraction column E. The bisulfitation reaction takes place in R which is of sufficient capacity to provide a residence time of about 15 to 30 minutes. The two-phase mixture in R, comprising an aqueous solution of alkali-metal bisulfite complex and a butanol solution of non-reacting impurities, overflows to separator S which is placed in an appropriate level with respect to extractor E and reactor R. All three vessels are vented to atmosphere at L which ensures that flow by gravity is maintained smoothly from R to S, and from S to tank C which receives the waste butanol extract containing impurities. The crude bisulfite complex which has separated in S returns, also by gravity, to a point at the top of the extraction column below the solvent interface. Here, it flows downwards and countercurrent to a stream of pure butanol supplied to the bottom of the column from tank A by metering pump $P_1$, feeding through the temperating exchange $H_1$. The pure bisulfite complex, denuded of non-reacting impurities, emerges from the bottom of the column from which it is metered by pump $P_2$, feeding to the product tank B. In this manner, a given small volume of solvent is used to perform a selective, polishing purification step on the bisulfite complex and then passes on to fulfill a second function in entraining grosser quantities of tarry impurities in the initial bisulfitation reaction. The system works as a single unit and may, in effect, be regarded as an extraction operation in which the first stage is accomplished separately and simultaneously with a chemical reaction.

While the preferred solvent is butanol, the invention is not restricted to one solvent. Other low density solvents may be used in the apparatus, provided that precautions are taken to strip the dissolved butanol from the sodium vanillinate solution prior to its introduction to reactor R, i.e. to avoid contaminating the second solvent with butanol.

In general the solvent must be non-reactive with all components of the aqueous phase being extracted, must adequately dissolve the unwanted tarry impurities and be a favorable extractant for the water-soluble impurities in the aqueous vanillin-bisulfite complex. Furthermore, it must be sufficiently insoluble in the aqueous phase to form a separable layer with minimum tendency to emulsion. Finally, it should be chemically stable and should preferably possess a boiling point in the approximate range 40° C to 140° C where recovery by distillation is most convenient. It is typified by the isomeric normal-, iso-, secondary-, and tertiary-butyl alcohols, by normal- and iso-amyl alcohols, and by the lower-boiling hexanols such as 4-methyl-2-pentanol.

The extractive bisulfitation process is not restricted to solvents which are less dense than water and modifications to the apparatus which are obvious to those skilled in the art would permit of the use of solvents which are denser than water. However, suitable dense solvents having all the required characteristics listed above are much less common than low-density solvents and may be regarded as relatively exotic and uncommercial.

From the purified solution of vanillin-bisulfite complex the vanillin may be recovered in any one of three ways. The complex may be cleaved by adding alkali, when the liberated vanillin may be extracted at its sodium salt into a solvent phase such as butanol. Or, more commonly, it may be cleaved by adding a mineral acid, whereupon sulfur dioxide is liberated and may be re-used for further bisulfitation. The vanillin is again extracted by means of a solvent. A third procedure is described by Otmar Toppel in German Pat. Nos. 1,119,244 (Dec. 14, 1961). In this, the complex is cleaved by heating in the presence of a solvent to temperatures above 50° C.

In our process, the preferred method of treating the purified solution of vanillin bisulfite complex is to add sufficient sulfuric acid so that, after stripping off both butanol and sulfur dioxide in steam, the final pH is 2.0 or lower. The presence of butanol is no longer required since the subsequent stage entails extraction with a different solvent. For quantitative recovery of vanillin from this dilute acidified solution of bisulfite complex it is important that sulfur dioxide also be completely removed. Any residual traces are sufficient to bind significant quantities of vanillin and render it inextractible in the following stage. The reaction is to some extent an equilibrium and only by complete removal of sulfur dioxide from the system can quantitative liberation of vanillin be achieved.

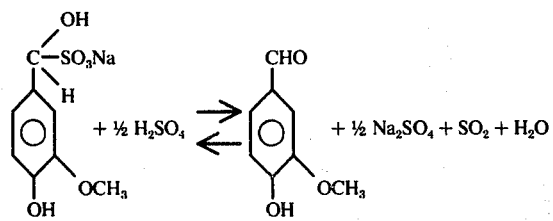

The exhaustive stripping in steam of both these volatile materials is a tedious and uneconomic operation if conducted batchwise, as may be comprehended from a study of the vapour-liquid equilibrium curves.

Figure 3:
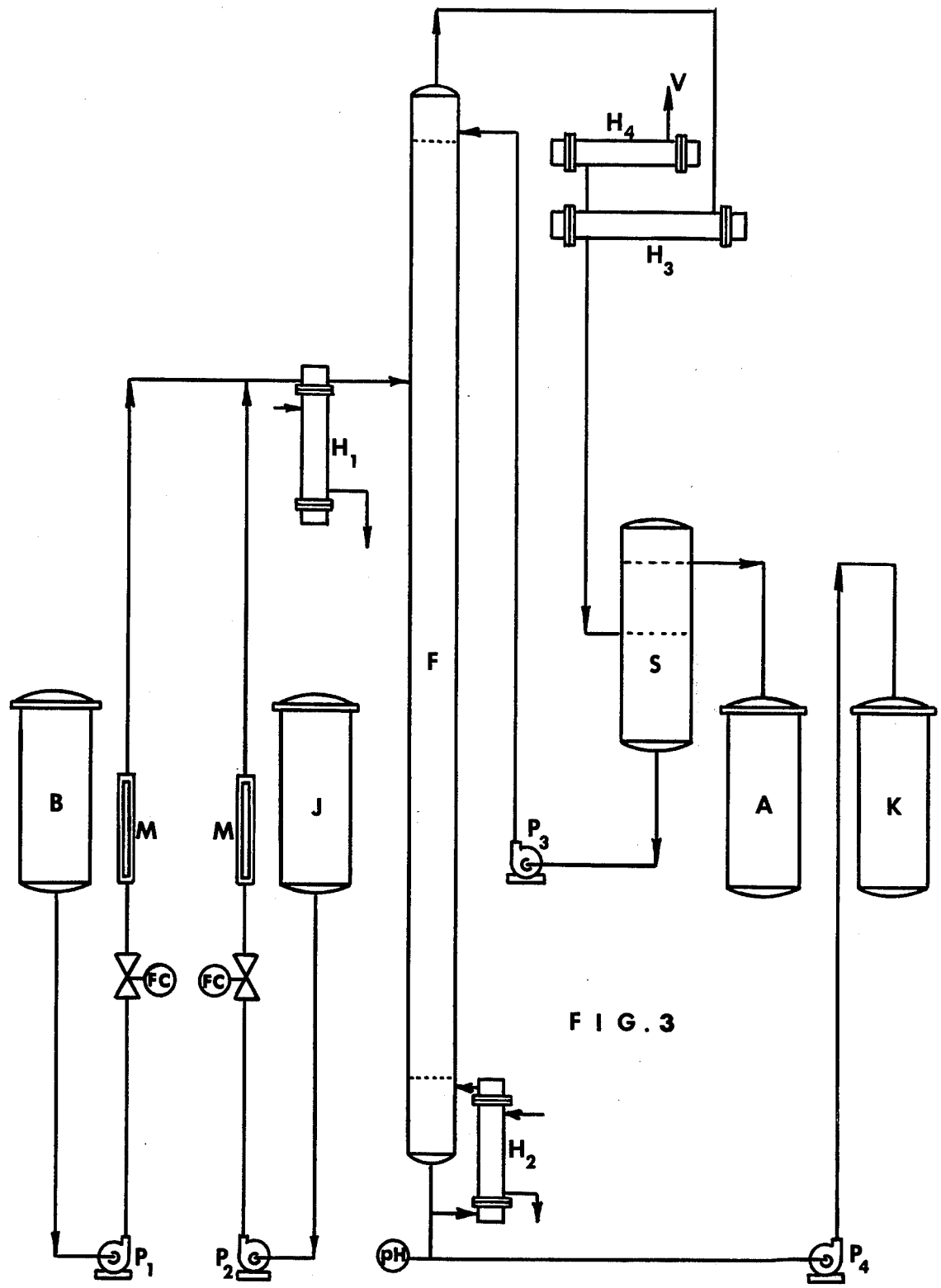
FIG. 3 is a flow diagram of another type of apparatus where a continuous fractionating still is employed subsequently to decompose the vanillin-bisulfite complex.

A more efficient separation may be accomplished in a continuous fractionating still in which the feed, in its downward travel through a column, encounters steam introduced at the bottom and is progressively denuded of its more volatile components, finally emerging from the bottom in a substantially volatile-free form. At this point, the decomposition of the bisulfite complex may be said to be complete, and not before. The continuous still therefore becomes an integral part of the decomposition reactor, as illustrated in FIG. 3, and the expenditure of entraining medium, in this case steam, is reduced to a minimum.

Besides steam, air or any other gas unreactive to the constituents may be used to strip the sulfur dioxide from the solution. However, in such cases butanol remains in solution and must be removed in a separate operation if the subsequent extraction step is to be performed with a different solvent. Gases used at ambient temperature are less sufficient for stripping than when used at the boiling temperature of the solution; hence steam has advantages in this respect.

The preferred method of our invention for decomposing the bisulfite complex is as follows. In FIG. 3, tank B is the storage vessel for complex prepared in the apparatus shown in FIG. 2. Tank J contains concentrated sulfuric acid. Both liquids are fed by metering pumps $P_1$ and $P_2$ through flow control valves FC and flowmeters M to a common line, where they are mixed. The combined liquids are preheated to the boiling point by preheater $H_1$ before entering at a position towards the top of stripping column F, which may be of packed, perforated plate, bubble cap, or any other conventional distillation design. The liquids flow to the bottom of the column where they are kept in a boiling state by reboiler $H_2$. Steam from these boiling still bottoms rises through the column, countercurrent to the liquid flow, progressively stripping out volatile solvent and sulfur dioxide, which concentrate in the upper part of the column. The proportion of sulfuric acid feed is adjusted so that the pH of the liquor discharged from the bottom of the column is kept at 2.0. This liquor, which now contains free vanillin in solution, is transferred by pump $P_4$ to storage in tank K. The top part of the column above the feed point is a rectifying section (or, in distillation parlance, an analyzing section), where solvent, or solent/water azeotrope, is separated from water. Vapours from the top of the column are condensed by means of exchangers $H_3$ and $H_4$. In the case of solvents which are no more than partially miscible with water, such as normal butanol, the condensate separates into two phases in separator S, the top layer of solvent overflowing to storage tank A, and the bottom aqueous layer being returned by metering pump $P_3$ as a reflux to the top of the column. Some sulfur dioxide remains in solution in the solvent in tank A and is recycled with it to the bisulfitation rection already illustrated in FIG. 2. The bulk of the sulfur dioxide is discharged from vent V, from where it too may be recycled to the bisulfitation reactor in lieu of fresh gas.

The product of this reaction is a dilute aqueous solution of vanillin accompanied by sodium sulfate in an acid medium. The vanillin is recovered therefrom by countercurrent extraction with a favorable water-immiscible organic solvent such as the hydrocarbons and halohydrocarbons, including toluene, benzene, xylene, or chloroform. The extracted aqueous solution is combined and neutralized with waste alkaline oxidate from the oxidation reactor. When the operation is situated in a kraft mill, as proposed in concurrently U.S. application, Ser. No. 413,912 of Donald B. Mutton et al., entitled "Lignin Oxidation Process", the combined waste liquors are returned for incorporation in the kraft mill recovery system to recover sodium and sulfur values. It is one of the features of our invention which makes it economically viable that not only the caustic soda which is added to the oxidation stage but also the sulfuric acid employed for decomposing the bisulfite complex may be credited to the vanillin plant for their equivalent value as salt cake. It is indeed that the make-up chemical for the kraft pulp mill contain both sodium and sulfur in stoichiometrically equal proportions. If the return to the mill comprised only the waste liquor from the oxidizer, i.e. containing only added sodium hydroxide, then it would be necessary to balance this by an equivalent addition or sulfur in some form or another to an appropriate stage of the mill recovery system. While the sodium- and sulfur-bearing chemicals used in our process are not of necessity balanced stoichiometrically any deficiency one way or another is sufficiently small to be easily corrected in the mill.

After bisulfite decomposition and extraction, the solution of vanillin in solvent is sufficiently pure to yield a crystalline mass of crude vanillin or evaporating the solvent and allowing to cool. Typically, this crude material contains the following constituents:

| | | |
|---|---|---|
| Vanillin | | 90.4% |
| ortho-Vanillin | | 1.3% |
| Acetovanillone | | trace |
| p-hydroxybenzaldehyde | | 0.3% |
| Syringaldehyde | | 0.3% |
| Guaiacol | less than | 1.0% |

In the industry, it is common practice to refine vanillin of this quality by further stages of vacuum distillation and crystallization from water. When these conventional techniques are applied to the crude product made by the methods described in our invention and which has a typical composition represented by the aforesaid analysis, a prime grade of vanillin results which is suitable for food flavouring.

DETAILED DESCRIPTION OF INVENTION

In order to disclose more clearly the nature of the present invention, the following examples illustrating the invention are given. It should be understood, however, that this is done solely by way of example and it is intended neither to delineate the scope of the invention nor limit the ambit of the appended claims. In the examples which follow, and throughout the specification, the quantities of material are expressed in terms of parts by weight, unless otherwise specified.

EXAMPLE 1

The following is an example of the purification process which employs the treatment we have termined extractive bisulfitation.

Ordinary solvent extraction in accordance with U.S. Pat. No. 2,104,701 was used to collect into normal butanol the vanillin from an oxidized kraft black liquor. The resulting butanol solution contained 0.75 grams per liter of vanillin. This was extracted in a countercurrent extraction column with water containing 3 grams per liter of sodium sulfate, using 1 liter of water for each 5 liters of butanol solution. Vanillin and butanol contents of the resulting aqueous solution were as follows:

| | |
|---|---|
| Vanillin (as sodium vanillinate), grams per liter | 3.71 |
| Butanol, % w/v | 6.8 |

This solution as submitted to the bisulfitation reaction under extractive conditions in the apparatus illustrated in FIG. 2, according to the following conditions:

| | |
|---|---|
| Aqueous sodium vanillinate feed, liters/hour | 4.8 |
| Water-saturated butanol (80% w/w), liters/hour | 1.2 |
| Sulfur dioxide, grams per hour | 9.0 |
| Temperature, ° C. | 25 |

Properties of the two streams were as follows:

| | Aqueous Bisulfite Complex | Butanol Extract |
|---|---|---|
| Flow rate, liters per hour | 4.8 | 1.2 |
| Specific gravity, 60° F | 1.009 | 0.856 |
| Total solids, grams per liter | 20.6 | 18.3 |
| Butanol, % w/v | 6.8 | 65.4 |
| Vanillin, grams per liter | 3.55 | 1.49 |
| Guaiacol, grams per liter | 0.1–0.2 | 0.1–0.2 |
| ortho-Vanillin, grams per liter | 0.34 | 0.1 |
| Acetovanillone, grams per liter | Nil | 2.94 |
| Syringaldehyde, grams per liter | Nil | 0.35 |

The butanol extract containing acetovanillone and other impurities was distilled to recover the solvent. The aqueous solution containing predominantly vanillin bisulfite complex was then submitted to a decomposition reaction using sulfuric acid as described hereinabove.

EXAMPLE 2

The following is an example of the continuous process in which the aqueous solution of vanillin bisulfite complex is decomposed.

In a plant run using equipment of the type illustrated in FIG. 3, the feed solutions had the following composition:

| | | |
|---|---|---|
| Tank B | Vanillin (as bisulfite complex), gram/liter | 1.72 |
| | n-butanol, % w/v | 6.2 |
| | Sulfur dioxide (including combined) grams/liter | 14.5 |
| | Total Solids, grams/liter | 25.5 |
| | pH | 4.5 |
| Tank J | Sulfuric acid, grams per liter | 218 |

These solutions were fed into the apparatus at the rate of 3 liters per hour of bisulfite complex and 0.24 liter per hour of acid. A little supplementary steam was fed into the kettle at the bottom of the column. In separator S, a two-phase distillate was collected at the following rates:

| | |
|---|---|
| Upper layer (wet butanol), liters/hour | 0.24 |
| Lower layer (solution of butanol in water), liters/hour | 0.61 |

Product at the base of the column was discharged at 3.6 liters per hour and had the following composition:

| | |
|---|---|
| Free vanillin, grams per liter | 1.60 |
| Sulfur dioxide, grams per liter | 0.04 |
| n-butanol, % w/v | 0.5 |
| pH | 2.05 |

EXAMPLE 3

The following is an additional example of the continuous decomposition of vanillin-bisulfite complex with acid, using in this case air as a stripping agent.

An apparatus of the type illustrated in FIG. 3 was supplied with the following feed solutions:

| | | |
|---|---|---|
| Tank B | Vanillin (as bisulfite complex), grams/liter | 3.35 |
| | n-butanol, % w/v | 1.94 |
| | Sulfur dioxide (including combined), grams/liter | 11.6 |
| | Total solids, grams/liter | 33.0 |
| | pH | 4.2 |
| Tank J | Sulfuric acid, grams per liter | 218 |

These solutions were fed at the rate of 3.0 liters per hour of bisulfite complex to 0.4 liter per hour of acid. In this example, air at the rate of 15.4 cu. ft. per hour was used to strip the sulfur dioxide in place of steam. In consequence, most of the butanol remained in the product and no distillate was obtained. The product from the base of the column had the following composition:

| | |
|---|---|
| Vanillin, grams per liter | 2.88 |
| Sulfur dioxide, grams per liter | 0.01 |
| n-butanol, % w/v | 1.37 |
| pH | 1.1 |

The terms and expressions which have been employed are used as terms of description and not of limitation, and there is no intention in the use of such terms and expressions of excluding any equivalents of the features shown and described or portions thereof, but is it recognized that various modifications are possible within the scope of the invention claimed.

What is claimed is:

1. A purification process for separating vanillin from related phenolic impurities in which an aqueous alkaline solution of vanillin and said related phenolic impurities is treated with sulfur dioxide or an acidic salt of sulfurous acid to form the bisulfite addition complex of vanillin and to adjust the pH in the range 3.0 to 4.5, which treatment is conducted in the presence of a water-immiscible alcohol selected from the class consisting of normal-, iso-, secondary-, and tertiary-butyl alcohols, normal-, and iso-amyl alcohols and 4-methyl-2-pentanol, in order to extract non-reacting tarry impurities deposited during the acidification, separating the said water-immiscible alcohol layer formed, removing the remaining aqueous phase to an extraction zone where the aqueous solution of vanillin-bisulfite complex is subjected to extraction with fresh said water-immiscible alcohol to remove water-soluble, non-reacting impurities, the said alcohol extract of impurities being then separated and returned to treatment with sulfur dioxide or an acid salt of sulfurous acid, where it entrains and dissolves unwanted tarry impurities deposited during acidification, acidifying said aqueous solution by the addition of acid to cleave the bisulfite addition complex of vanillin, leaving the vanillin in said aqueous solution substantially free from said related phenolic impurities and thereby separating said vanillin from said related phenolic impurities.

2. A process according to claim 1 wherein the said alcohol extract is finally separated for recovery of the said alcohol by distillation.

3. A process according to claim 1 in which the said water-immiscible alcohol is normal-butanol.

4. A process according to claim 1 which is continuous.

5. A process according to claim 1 wherein the extraction with the said water-immiscible alcohol is carried out counter-currently.

6. A process in accordance with claim 1 in which the vanillin-bisulfite complex formed by the treatment with sulfur dioxide or an acid salt of sulfurous acid is cleaved in aqueous solution by the addition of a mineral acid and the acidified solution is contacted in countercurrent flow with a gas selected from the class consisting of air and steam to remove the liberated sulfur dioxide and complete the cleavage reaction.

7. A process of claim 6 in which the mineral acid is sulfuric acid.

8. A process according to claim 6 which is continuous.

9. A process according to claim 6 wherein the gas is steam.

* * * * *

UNITED STATES PATENT AND TRADEMARK OFFICE
CERTIFICATE OF CORRECTION

PATENT NO. : 4,021,493
DATED : May 3, 1977
INVENTOR(S) : Frederick William Major; Francois Marcel André Nicolle It is certified that error appears in the above-identified patent and that said Letters Patent are hereby corrected as shown below:

Column 1, line 11, correct the spelling of "hydroxybenzaldehyde"
Column 2, line 6, after "suitable is" delete "that".
Column 2, line 54, correct the spelling of "aldehydic".
Column 3, line 3, after "impurities" insert "precipitate".
Column 3, line 10, correct the spelling of "bisulfite".
Column 4, line 40, amend "emulsion" to read "emulsification".
Column 5, line 49, amend "sufficient" to read "efficient".
Column 6, line 8, correct the spelling of "solvent".
Column 6, line 18, correct the spelling of "reaction".
Column 6, line 42, after "indeed" insert "necessary".
Column 6, line 48, amend "or" to read "of".
Column 6, line 57, amend "or" to read "on".
Column 7, line 23, correct the spelling of "termed".
Column 7, line 41, amend "as" to read "was".

Signed and Sealed this

Fifteenth Day of May 1979

[SEAL]

Attest:

RUTH C. MASON
Attesting Officer

DONALD W. BANNER
Commissioner of Patents and Trademarks